United States Patent [19]

Millikan et al.

[11] Patent Number: 4,971,041
[45] Date of Patent: Nov. 20, 1990

[54] SPLINT APPARATUS

[76] Inventors: Michael E. Millikan; Mary Jane Millikan, both of 4414 Beaver Ave., Fort Wayne, Ind. 46807; Mary Mattingly, 6024 Wayne Trace, Fort Wayne, Ind. 46816

[21] Appl. No.: 422,677

[22] Filed: Oct. 17, 1989

[51] Int. Cl.⁵ ............................ A61F 5/04; A61F 3/37
[52] U.S. Cl. .................................... 128/87 R; 128/88; 128/878
[58] Field of Search ............... 128/87 R, 87 A, 88, 128/89 A, 90, 91 R, 878, 879, 877, 155, 156, 157

[56] References Cited

U.S. PATENT DOCUMENTS

| | | | |
|---|---|---|---|
| 1,916,789 | 7/1933 | Fordham | 128/87 R |
| 2,373,802 | 4/1945 | Anderson | 128/90 |
| 2,468,580 | 4/1949 | Weis | 128/87 R |
| 2,692,596 | 10/1954 | Marconnet | 128/91 R |
| 2,823,668 | 2/1958 | Court | 128/87 R |
| 3,521,623 | 7/1970 | Nichols | 128/DIG. 20 |
| 3,548,819 | 12/1970 | Davis | 128/DIG. 20 |
| 3,903,878 | 9/1975 | Spann | 128/77 |
| 3,911,497 | 10/1975 | Lewis, Jr. et al. | 2/16 |
| 3,939,829 | 2/1976 | Spann | 128/878 |
| 3,955,565 | 5/1976 | Johnson, Jr. | 128/DIG. 20 |
| 4,078,560 | 3/1978 | Hill | 128/881 |
| 4,168,063 | 9/1979 | Rowland | 128/DIG. 20 |
| 4,219,892 | 9/1980 | Rigdon | 128/DIG. 20 |
| 4,276,875 | 7/1981 | Sandegard | 128/89 R |
| 4,378,009 | 3/1983 | Rowley | 128/DIG. 20 |
| 4,465,064 | 8/1984 | Boone | 128/88 |
| 4,483,332 | 11/1984 | Rind | 128/89 R |
| 4,573,456 | 3/1986 | Spann | 128/80 R |
| 4,657,003 | 4/1987 | Wirtz | 128/869 |
| 4,766,890 | 8/1988 | Hollrah | 128/89 R |
| 4,788,972 | 12/1988 | DeBusk | 128/89 R |

OTHER PUBLICATIONS

Posey Patient Safety Aids—1988 Product Line.

*Primary Examiner*—Robert A. Hafer
*Assistant Examiner*—Michael Brown
*Attorney, Agent, or Firm*—Jeffers, Hoffman & Neiwyk

[57] ABSTRACT

An apparatus for supporting and protecting a limb of a patient. The apparatus includes a plurality of elongated cushioned tubes which are connected together to form a cushioning wrap. At least two of the tubes are separated by a web of material. The web may be formed of a mesh material. Stiffening rods are removably received in pockets formed on the outside of at least one of the tubular elements. A fastening device is provided to hold the apparatus in place after it is wrapped about the limb of a patient. Provision may be made for heat/ice packs by providing pockets on the inside of the wrap.

19 Claims, 2 Drawing Sheets

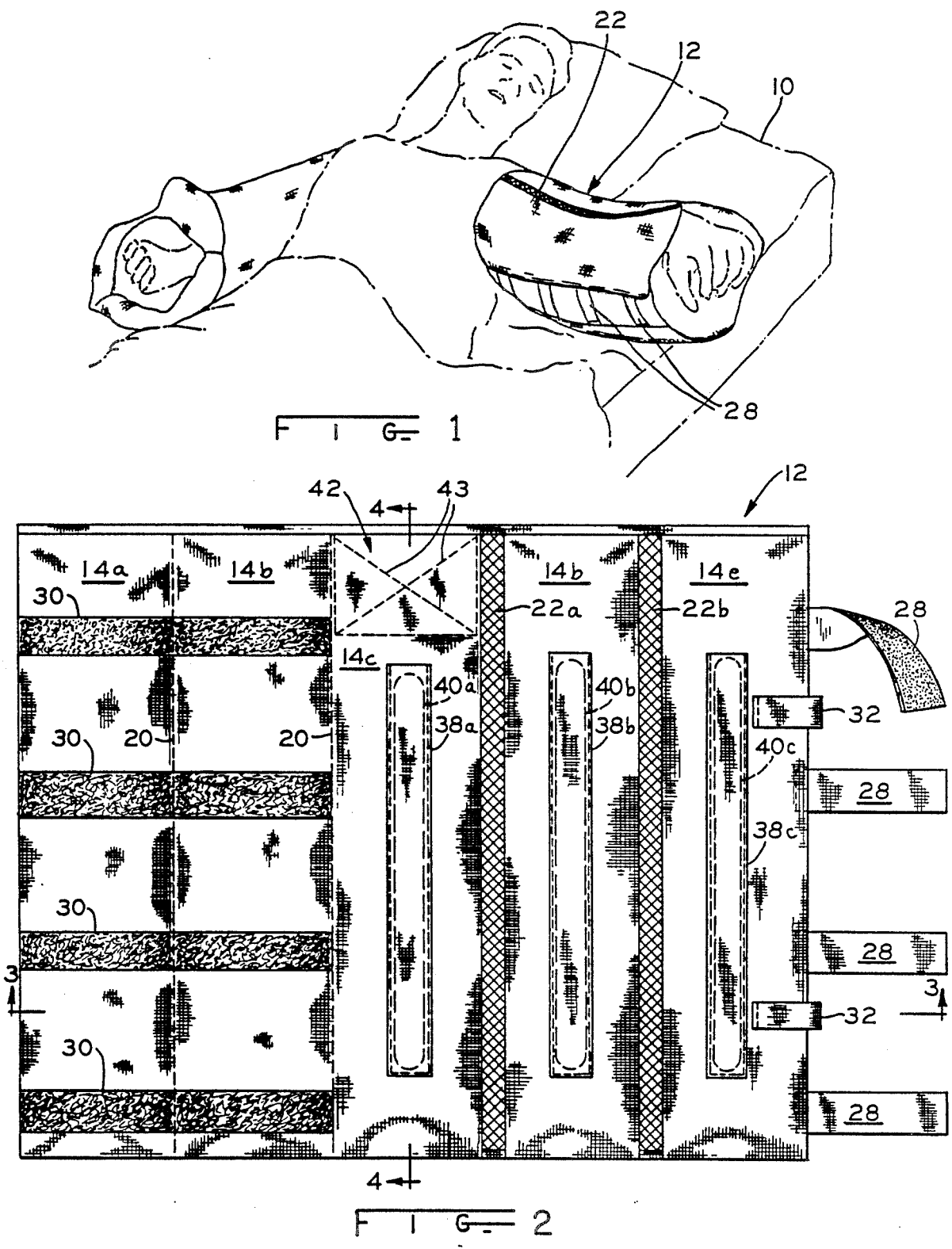

SPLINT APPARATUS

BACKGROUND OF THE INVENTION

This invention relates to a splint apparatus and in particular to a cushioned splint apparatus for protecting and supporting the limbs of a patient or for immobilizing an injured limb.

Many patients, such as accident victims who are confined to hospital beds, including comatose patients, need support for their limbs to prevent muscle contracture. If a limb is not supported but is permitted to drop, the muscles of the limb tend to contract, thus deforming the limb and causing it to curl up and resulting in the need for special rehabilitation to correct the contracted condition of the limb.

Some prior art devices have been provided for supporting limbs of patients. These devices have been unsatisfactory since they have not adequately protected limbs from contraction and furthermore because they have tended to result in injury to the patient's skin as they block air circulation to the skin and prevent the skin from breathing. Such prior art devices comprise, for instance, wrist sleeves which may be padded or formed of a resilient material and which include tie down straps to tie a patient's limbs to the rails of the bed on which the patient is confined. Since these devices do not prevent bending of the limb, they have not prevented muscle contracture. These prior art devices also left part of the limb unprotected which resulted in sheet burns and caused the unprotected portion of the limb to become too cold or to become injured from contact with hard surfaces such as the bed frame and the like. Also because of the need to tie these devices to the bed, the patient, even a comatose patient, resists such restriction and this results in further contraction and deterioration of the limbs of the patient. Lastly, the prior art wrist sleeves have not been capable of use with intravenous and catheter devices so that such devices needed to be removed in order to accommodate the tubings which must be used with intravenous feeding equipment, catheters and the like.

A need also exists for an athletic splint apparatus for immobilizing injured limbs of athletes and for a splint apparatus which is convenient to wrap about an injured limb and to apply an ice pack or a heat pack to the limb.

Accordingly it is desired to provide a splint apparatus to immobilize limbs and to inhibit the limbs from bending to prevent muscle contracture and to prevent or decrease muscle atrophy. It is also desired to provide such an apparatus which is soft and protects limbs from hard surfaces while permitting the patient's skin to breathe while preventing the limb to become cold. It is further desired to provide such an apparatus which is compatible with the use of tubings for catheters and the like. Lastly, it is desired to provide such an apparatus to enable immobilization of limbs and convenient application of ice packs or heat packs to limbs.

SUMMARY OF THE INVENTION

The present invention, in one form thereof, comprises a plurality of parallel tubular cushions which are connected together in an array to form a cushioned apparatus which may be wrapped around a limb to immobilize and protect the limb. At least two of the tubular cushions are spaced apart and are connected together by means of a flexible web. The web may be perforated or form a mesh. A fastening device is provided whereby the apparatus is retained in place around the limb.

The present invention, in one form thereof, comprises an array of soft cushioning elongated cylindrical or tubular elements which are connected together in an array. At least two of the cushioning elements are spaced apart and are connected together by means of a strip of flexible material which may be perforated. The apparatus may be wrapped around a limb and retained in place by means of fasteners. At least one of the tubular elements has a stiffening member secured thereto whereby the entire apparatus resists bending in the longitudinal direction. Lastly, pockets may be provided on the device for receiving ice or heat packs whereby the apparatus may be wrapped about a limb with the ice or heat packs applied to the limb to aid in treating an injury to the limb.

An advantage of the apparatus according to the instant invention is that it prevents or reduces muscle contracture for convalescing patients. The apparatus according to the present invention may include perforated or meshed webbing which permits air to pass therethrough and therefore permits the skin of the limb to breathe, thereby preventing skin breakdown. Additionally, since the apparatus surrounds the entire limb, it protects the limb from hard surfaces and also protects the limb from experiencing "sheet burn". The apparatus also protects exposed limbs, thus serving as a covering to warm them.

The apparatus is easily attached to and removed from a limb. Furthermore, the apparatus permits the use of tubing for intravenous feeding and catheters or the like by providing spaces for the tubings between the cushioning elements to accommodate the tubings. This also keeps the patient from removing the tubings and thereby causing further injury.

Since the apparatus is easily attached to a limb or removed therefrom, it is ideally suited to be used in connection with athletic injuries. The apparatus is useful for immobilizing an injured limb and therefore prevents further injury from occurring to the limb until proper medical attention can be given to the injury. Furthermore, by applying ice packs or heat packs to an injured limb shortly after occurrence of the injury on the athletic field, quick treatment of the injury is effected thereby reducing convalescing time for the athlete.

By virtue of preventing contraction of the limbs, the apparatus may shorten rehabilitation time. The apparatus is adjustable and can therefore be used on limbs of various sizes. Lastly, by manufacturing the apparatus of suitable materials, the apparatus is easily washable and cleanable.

The present invention, in one form thereof, comprises a splint apparatus for supporting and protecting a limb. The splint apparatus includes a plurality of generally parallel elongated cushioning elements and means for connecting the cushioning elements along their respective longitudinal sides to form a segmented cushioned wrap. At least two of the cushioning elements are spaced apart and are interconnected by means a web which has respective ends thereof secured to respective longitudinal sides of the two cushioning elements and separates those elements. Means are also provided for securing the segmented cushion wrapped around a limb.

The present invention, in one form thereof, comprises a splint apparatus for wrapping about a limb. The apparatus includes a generally parallel array of elongated cushioning elements. At least two of the cushioning elements are spaced apart. A strip of flexible perforated material interconnects respective opposed sides of the spaced apart elements. Fastening means are provided for securing the array wrapped around the limb.

The present invention, in one form thereof, comprises a splint apparatus for use in supporting and protecting a limb. The apparatus includes a plurality of parallel tubular cushioning interconnected elements forming a segmented cushion. At least two of the cushioning elements are spaced apart and are interconnected by a flexible mesh web. Stiffening means are secured to at least one of the cushioning elements. Means are provided for fastening the apparatus around a limb.

It is an object of the present invention to provide an apparatus for encasing a limb and keeping the limb rigid while protecting the limb from injury, from becoming chilled, and from skin deterioration. It is also an object to provide such an apparatus wherein rigidity is adjustable by the selective addition or deletion of stiffening devices.

It is a further object of the present invention to provide an apparatus which accommodates the use of intravenous or catheter tubes without restricting flow therethrough.

It is still another object of the present invention to provide an apparatus which reduces and prevents muscle contracture in limbs of bed ridden patients.

Still a further object is to provide an apparatus which may be quickly and easily secured to a limb or removed therefrom and which is easily cleanable.

BRIEF DESCRIPTION OF THE DRAWINGS

The above mentioned and other features and objects of this invention, and the manner of attaining them, will become more apparent and the invention itself will be better understood by reference to the following description of the embodiments of the invention taken in conjunction with the accompanying drawings, wherein:

FIG. 1 is a perspective view of the splint apparatus according to the present invention in use on the arms of a patient;

FIG. 2 is a top plan view of the splint apparatus according to the present invention;

Corresponding reference characters indicate corresponding parts throughout the several views of the drawings.

The exemplifications set out herein illustrate a preferred embodiment of the invention, in one form thereof, and such exemplifications are not to be construed as limiting the scope of the disclosure or the scope of the invention in any manner.

DESCRIPTION OF THE PREFERRED EMBODIMENT

Figure 3:
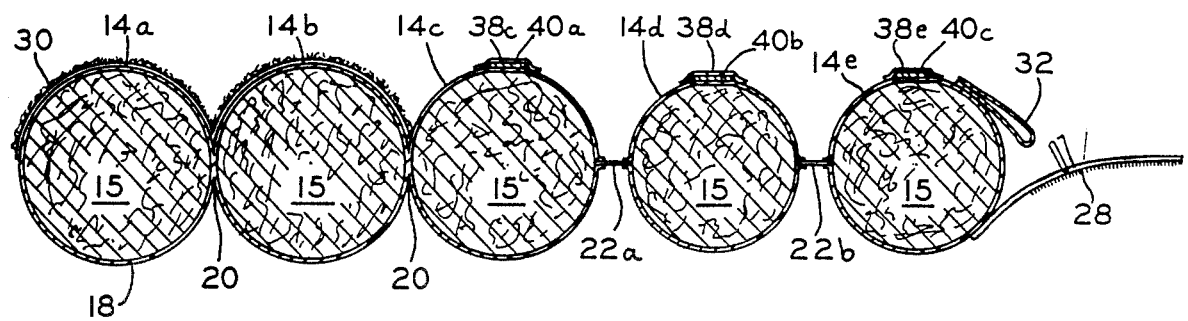
FIG. 3 is a cross sectional view of the splint apparatus of FIG. 2 taken along lines 3—3 thereof.

Referring now to FIGS. 1-4, there is shown a patient reclining on a bed 10 and having a splint apparatus 12 wrapped about each arm to protect and support both arms. Splint apparatus 12 includes five cushioning elements 14a-14d as best seen in FIG. 3. It should be noted that more or less of such cushioning elements may be provided as desired. The cushioning elements shown in this embodiment are tubes which are filled with soft stuffing material. As shown in FIG. 2, tubes 14a, 14b, and 14c may be formed as a unit from an outer cover 16 and an inner cover 18. The outer and inner covers are stitched together along lines 20, as best seen in FIG. 2, to form tubes 14a, 14b, and 14c. However, in the disclosed embodiment, tubes 14d and 14e are formed as separate tubes. Tube 14d is secured to tube 14c by means of a strip of webbing material 22a. Similarly, tubes 14d and 14e are connected together by means of a strip of webbing material 22b. The material from which the tubes 14 are made should be non-harmful to skin and is preferably absorbent. Suitable materials for constructing tubes 14 are cotton or a polyester/cotton mix which are readily commercially available. Webbing material 22 should be flexible to permit the apparatus 12 to be wrapped around a limb. The webbing material 22 may be formed of the same material as tubes 14. However, it has been found that webbing material 22 may also be perforated or meshed. This permits air to circulate over the skin of the patient thereby permitting the skin to "breathe" and thereby reducing potential damage to the skin. It should be noted that, if desired, webbing material 22 could be provided between each respective tube 14a-14e or only between two adjacent tubes. Applicants have found that the use of a nylon mesh screen material similar to that used in the construction of tents is suitable. It should be noted that the width of the webs may be varied, depending upon the need for air circulation. Furthermore, the mesh size may be varied depending upon strength requirements for the apparatus and the like. The length of tubes 14 may vary but is preferably sufficiently long so that, in the case of an arm splint, the patient will not be able to bend either his elbow or his wrist, thereby preventing muscle contracture and preventing damage to the ligaments and muscles of the patient's limbs. It should also be noted that, while the apparatus is shown for use on a patient's arm, the apparatus is equally suitable for use on a patient's legs. In the use of the apparatus on a patient's leg, it can be constructed to support a patient's foot to eliminate or reduce "foot drop" in bed-ridden patients.

In effect, apparatus 12 forms a cushioned wrap for wrapping around a limb. By referring to FIG. 3, the cushioned wrap 12 is formed as a generally planar and flexible assembly and is formed of individual cushioning elements which are secured together. The cushioning elements are spaced apart and are secured to each other by webs 22. It is readily apparent that webbing material could be secured between each of the tubes 14 or between only three of the tubes 14 as shown in FIG. 3 or even between only two of the tubes. Furthermore, while the stuffing material 15 should be soft to provide proper cushioning of the limb, various types of stuffing could be used such as various man-made materials including polyfill and Ensolite.

In order to secure the apparatus around a patient's limbs, fastening means are provided. In the disclosed embodiment, straps 28 and 30 are provided which comprise hook and loop material also sold under the name Velcro. Thus the entire apparatus may be wrapped around a patient's limb, strap 28 is then placed over strap 30 to secure the hook and loop material together to retain the splint apparatus 12 wrapped about the patient's limb. A pair of tie-down loops 32 are provided so that the splint apparatus 12 may be anchored to the bed with a tie down string, thereby preventing the patient from unduly moving his limbs and thereby injuring himself and possibly causing IV tubes and the like to become disconnected.

While, in the preferred embodiment of FIGS. 1-3, hook and loop fasteners have been shown, many types of fasteners could be used to secure the apparatus around a patient's limb as further described hereinbelow in connection with FIG. 5.

It is readily apparent that the cushioned splint apparatus 12 prevents the patient from harming himself and prevents injuries to limbs from hard surfaces or from constant contact of sensitive skin with sheets or blankets.

In order to provide the apparatus with greater stiffness to provide a more rigid splint apparatus for further reducing muscle contracture, one or more pockets 38 may be provided in which a stiffeners 40 are received. The pockets may be provided on the exterior surface of the apparatus. Stiffeners 40 may be formed of wood, plastic or other suitable material and may be somewhat shorter than tubes 14. Use of stiffeners 40 greatly reduces a patient's ability to bend his limb. As required, one or more stiffeners 40a, 40b, or 40c may be inserted in the respective pockets 38a, 38b, 38c to provide more or less rigidity for splint apparatus 12.

Figure 4:
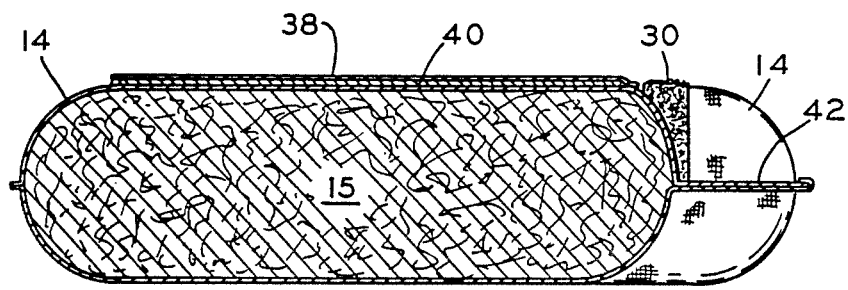
FIG. 4 is a cross sectional view of the splint apparatus of FIG. 2 taken along lines 4—4 thereof.

Referring to FIGS. 2 and 4, it can also be seen that a flat section 42 is provided in one end of tube 14c whereby tube 14c is shorter than tubes 14a, 14b, 14d and 14e. When the apparatus is in use, this flat section 42 may be arranged on the inside of the apparatus adjacent a patient's arm to reduce interference of the apparatus 12 with normal movement of the injured or protected limb. Thus section 42 would be located at the patient's armpit. Section 42 is shown as including stitchings 43 to thereby form a quilted section 42.

Figure 5:
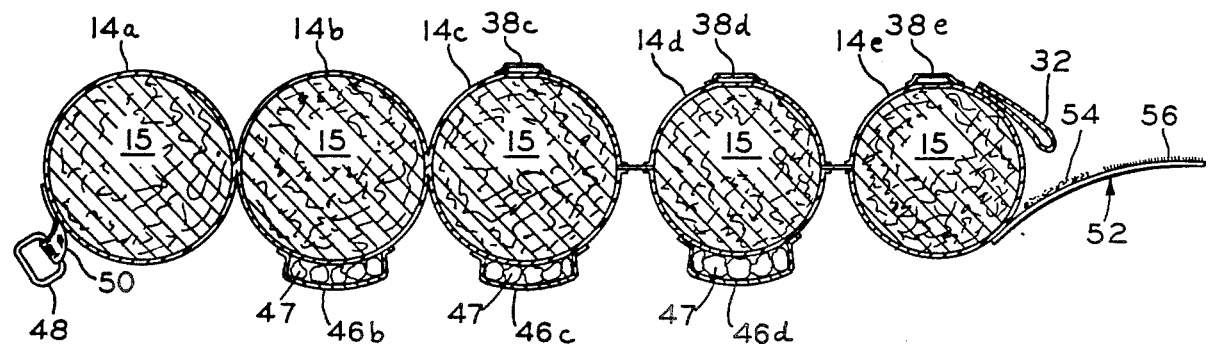
FIG. 5 is a cross sectional view of an alternative embodiment of the invention.

In an alternative embodiment shown in cross section in FIG. 5, pockets 46 have been provided on the interior surface of splint apparatus 12. These pockets 46 serve for receiving either ice or heat packs 47 as needed for treatment of an injury. Thus the ice/heat packs would be located close to the patient's skin. The pockets 46 are open ended to receive the ice/heat packs. A splint apparatus constructed in accordance with FIG. 5 is particularly useful for athletic injuries whereby a sprained or injured limb can be immediately treated on the athletic field by wrapping the limb and protecting it from bending and further injury, and for treating the injured limb with ice/heat packs to reduce swelling and to aid in healing of the injury.

Additionally, in the embodiment of FIG. 5, the fastening means consists of a strap 52 including sections of both hook and loop material thereon. Strap 52 may be pulled through a ring 48 which is secured to tube 14a by means of a strap 50. Strap 52 is thus folded back upon itself whereby the hooks and loops engage to securely fasten the apparatus.

It should, of course, be understood that many variations in the design are possible without departing from the scope or spirit of the invention. Thus, various materials may be used both for the tubes 14 and the stuffing 15, and various types of fasteners may be used to fasten the apparatus around the limb of a patient. It should also be understood that the splint apparatus is useful not only for use on the arms of a patient but are also very useful for protecting a patient's legs and for treating leg injuries. Additionally, the splint apparatus can be used to prevent "foot drop" by wrapping the device around a patient's ankle and by using a rigid support for the foot to prevent the foot from dropping and thereby causing muscle contracture. The apparatus may be formed in various lengths depending upon the size of the patient with whom it is used and furthermore may be made of various materials.

While this invention has been described as having a preferred design, it will be understood that it is capable of further modification. This application is therefore intended to cover any variations, uses, or adaptations of the invention following the general principles thereof and including such departures from the present disclosure as come within known or customary practice in the art to which this invention pertains and fall within the limits of the appended claims.

What is claimed is:

1. A splint apparatus for supporting and protecting a limb comprising:
    a plurality of generally parallel elongated cushioning elements;
    means for connecting said cushioning elements along their respective longitudinal sides to form a segmented cushioned wrap;
    a perforated web means for enabling circulation of air through said apparatus, said web means having respective ends thereof secured to and separating respective longitudinal sides of two said elements; and
    means for securing said splint apparatus around a limb.

2. The apparatus according to claim 1 wherein said web means comprises a strip of flexible mesh material.

3. The apparatus according to claim 1 including an elongated rigid member secured to one said cushioning elements.

4. The apparatus according to claim 1 wherein one of said cushioning elements includes an elongated pocket, an elongated rigid member disposed in said pocket.

5. The apparatus according to claim 1 wherein said securing means comprises strips of hook and loop material.

6. The apparatus according to claim 1 wherein said cushioning elements comprise tubes of fabric material, said tubes having soft stuffing material located therein.

7. The apparatus according to claim 1 wherein one of said cushioning elements includes a flattened portion.

8. A splint apparatus for wrapping about a limb, said apparatus comprising:
    a generally parallel array of tubular cushioning elements, at least two said cushioning elements being spaced apart;
    a strip of flexible perforated material interconnecting respective opposed sides of at least two said spaced apart elements to permit ventilation of the interior of said apparatus; and
    fastening means for securing said array around a limb.

9. The apparatus according to claim 8 wherein said material comprises mesh material.

10. The apparatus according to claim 8 including stiffening means secured to said array for providing rigidity for said array.

11. The apparatus according to claim 8 wherein one of said stiffening means comprises an elongated rigid member removably secured to one of said cushioning elements.

12. The apparatus according to claim 8 wherein said fastening means comprises hook and loop fastening strips.

13. The apparatus according to claim 8 wherein said cushioning elements comprise tubular fabric pockets having soft stuffing material disposed therein.

14. The apparatus according to claim 8 wherein one end of one of said tubular elements includes a flattened portion.

15. The apparatus according to claim 8 including securing means for securing said apparatus to a preselected support.

16. A splint apparatus for use in supporting and protecting a limb, said apparatus comprising:
   a plurality of parallel tubular cushioning interconnected elements forming a segmented cushioned wrap;
   at least two said cushioning elements being spaced apart and being interconnected by a flexible mesh web to permit ventilation of the interior of said apparatus;
   stiffening means secured to at least one of said cushioning elements; and
   means for fastening said apparatus around a limb.

17. The apparatus according to claim 16 wherein said flexible mesh web comprises nylon screening material.

18. The apparatus according to claim 16 wherein said stiffening means comprises a pocket located on one of said cushioning elements and an elongated rigid member removably received in said pocket.

19. The apparatus according to claim 16 wherein said fastening means comprises hook and loop fastening strips.

* * * * *